(12) United States Patent
Hobeika et al.

(10) Patent No.: US 11,207,108 B2
(45) Date of Patent: Dec. 28, 2021

(54) SURGERY PLANNING TOOL FOR SPINAL CORRECTION ROD

(71) Applicant: EOS IMAGING, Paris (FR)

(72) Inventors: Joe Hobeika, Paris (FR); David Invernizzi, Besancon (FR); Arnaud Grivet, Besancon (FR)

(73) Assignee: EOS IMAGING, Paris (FR)

( * ) Notice: Subject to any disclaimer, the term of this patent is extended or adjusted under 35 U.S.C. 154(b) by 169 days.

(21) Appl. No.: 16/607,072

(22) PCT Filed: May 3, 2017

(86) PCT No.: PCT/IB2017/000695
§ 371 (c)(1),
(2) Date: Oct. 21, 2019

(87) PCT Pub. No.: WO2018/203100
PCT Pub. Date: Nov. 8, 2018

(65) Prior Publication Data
US 2020/0375636 A1 Dec. 3, 2020

(51) Int. Cl.
A61B 17/70 (2006.01)
A61B 90/94 (2016.01)
A61F 2/46 (2006.01)
A61B 90/00 (2016.01)
A61B 17/00 (2006.01)

(52) U.S. Cl.
CPC ...... *A61B 17/7074* (2013.01); *A61B 17/7011* (2013.01); *A61B 90/94* (2016.02); *A61F 2/4684* (2013.01); *A61B 2017/00526* (2013.01); *A61B 2090/0807* (2016.02); *A61B 2090/376* (2016.02)

(58) Field of Classification Search
CPC ............. A61B 17/7074; A61B 17/7002; A61F 2/4684
See application file for complete search history.

(56) References Cited

U.S. PATENT DOCUMENTS

| 5,658,286 A | 8/1997 | Sava | |
| RE42,226 E * | 3/2011 | Foley | A61B 34/20 |
| | | | 600/426 |
| 2004/0117015 A1 | 6/2004 | Biscup | |
| 2009/0261505 A1 | 10/2009 | Patterson et al. | |
| 2009/0270922 A1 | 10/2009 | Biedermann et al. | |
| 2012/0172700 A1* | 7/2012 | Krishnan | G16H 30/20 |
| | | | 600/407 |
| 2014/0316420 A1* | 10/2014 | Ballard | A61B 17/7002 |
| | | | 606/102 |
| 2014/0350602 A1* | 11/2014 | Seme | A61B 17/7043 |
| | | | 606/250 |

FOREIGN PATENT DOCUMENTS

| EP | 3527154 A1 * | 8/2019 | ......... A61B 17/7049 |
| WO | WO-2015054543 A1 * | 4/2015 | ......... A61B 17/8863 |

OTHER PUBLICATIONS

International Search Report and Written Opinion, corresponding International Application No. PCT/IB2017/000695, dated Jan. 17, 2018.

* cited by examiner

*Primary Examiner* — Christian A Sevilla
(74) *Attorney, Agent, or Firm* — Marshall, Gerstein & Borun LLP

(57) ABSTRACT

This invention relates to a surgery planning tool, which is not a patient implant, comprising an elongated body including at least a portion having the shape and the size of a spinal correction rod.

1 Claim, 7 Drawing Sheets

SURGERY PLANNING TOOL FOR SPINAL CORRECTION ROD

CROSS REFERENCE TO RELATED APPLICATIONS

This application is the U.S. National Phase of International Patent Application No. PCT/IB2017/000695 filed May 3, 2017, the disclosure of which is incorporated herein by reference in its entirety.

FIELD OF THE INVENTION

The invention relates to the field of spinal correction rod, preferably to correct patient scoliosis.

BACKGROUND OF THE INVENTION

In the specific case of spinal arthrodesis surgery applied to treat scoliosis or degenerative spine deformations most of the surgeons are used to cut and bend the rods directly during the surgery for long segment spinal fixations.

The surgeons usually have to apply successive in situ corrections to the shape of the rods and to make some X-ray radiographic images to check the spinal correction.

According to a first prior art, in the field of spinal correction rod, it is known to plan, with planning software, the shape and the size of a spinal correction rod to be used as an implant within the body of a patient.

The shape and the size of this spinal correction rod implant is the output of the planning software. This output is under the form of a predetermined and organized set of numerical values being representative of the shape and the size of this planned spinal correction rod implant.

The surgeon receives both a long and straight metal rod and a paper containing this set of numerical values representative of the shape and the size of this planned spinal correction rod implant. After reading this set of numerical values representative of the shape and the size of this planned spinal correction rod implant, the surgeon has in mind the size and the shape of the desired spinal correction rod implant, and the surgeon cuts the received rod to make it have the right size, and then bends it to make it have the right shape, to get at the desired spinal correction rod implant having both the right size and the right shape.

According to a second prior art, in the field of surgery implant cutting tools, in knee prosthesis for example, it is known to make a personalized cutting tool, helping the surgeon to cut part of patient bone, in order to better (in a more personalized way) implement the personalized implant in the body of the patient. This field of the second prior art, dealing with personalized surgery cutting tool helping the surgeon when implementing a implant, is quite different from the spinal correction rod tool field of the invention helping to better shape and size the spinal correction rod implant to be implemented in the patient body.

This shaping and sizing is made essentially before spinal correction rod implant implementation, and not during prosthesis implementation. This spinal correction rod implant is a help to an existing organ, the patient spine, and not a partial or total replacement part of a patient organ, like a patient knee articulation. Both these preceding differences make the second prior art field rather irrelevant and far away for the man skilled in the art of the first prior art.

SUMMARY OF THE INVENTION

The object of the present invention is to alleviate at least partly the above mentioned drawbacks.

More particularly, the invention aims to provide a surgery planning tool helping the surgeon to implement a spinal correction rod implant in a patient body, such surgery planning tool being simple and efficient to use for the surgeon, and presenting a better compromise between simplicity and efficiency than the old paper containing merely a set of numerical values representative of the spinal correction rod implant did. This surgery planning tool will be a real tool helping directly the surgeon, and not only processing instructions to the surgeon helping him indirectly by telling him how he should proceed when implementing the spinal correction rod implant in patient body.

This object is achieved with a surgery planning tool, being no patient implant, comprising an elongated body including: at least a portion having the shape and the size of a spinal correction rod.

This object is also achieved with a pair of surgery planning tools according to the invention, wherein one of said surgery planning tools has the shape and the size of a spinal correction rod adapted to be implemented on one side of patient spine whereas one of said surgery planning tools has the shape and the size of a spinal correction rod adapted to be implemented on the other side of patient spine. This way, both spinal correction rods, both implants may be implemented in patient body by the surgeon, using a pair of similar surgery planning tools, one per spinal correction rod implant, thereby doubling the global gain in simplicity and efficiency that is gained when using only a single tool for only one of the spinal correction rod implants.

Preferably, one of said surgery planning tools is over bended or under bended as compared to said patient implanted spinal correction rod implant. This way, the surgery planning tool corresponds more precisely to the spinal correction rod implant, not in its original shape, but in its final shape when implemented, thereby integrating the counter effort exerted by the patient spine when submitted to the straightening effort of the spinal correction rod implant. This more precise surgery planning tool will be even more useful to the surgeon.

This object is again achieved with a kit comprising: a surgery planning tool or a pair of surgery planning tools according to the invention, a printed document or an electronic document including patient specific spinal correction information corresponding to said surgery planning tool or to said a pair of surgery planning tools. This way, the surgeon has at her or his disposal, both the helping surgery planning tool making surgery simpler and more efficient for her or him, and also all or part of the set of numerical values representative of the spinal correction rod implant as in the first prior art. This is more secure, since it allows the surgeon to crosscheck both pieces of information in order to more easily detect any possible mistake.

This object is still achieved with a manufacturing method of a surgery planning tool having the shape and the size of a spinal correction rod but being no patient implant, comprising: a first step of making two 2D X-ray patient images, a second step of making a patient specific 3D spinal reconstruction from said two 2D X-ray patient images, a third step of determining a patient specific spinal correction, a fourth step of making a surgery planning tool or a pair of surgery planning tools, according to the invention, having the shape and the size of a patient specific spinal correction rod implant but being no patient implant. This way, manufacturing said surgery planning tool is first easier and second gets at a more personalized surgery planning tool, what is more efficient for the surgeon.

According to the invention, the proposed surgery planning tool aims at proposing a 3D template set to help the surgeons to apply a surgery planning correction in situ.

According to embodiments of the invention, no investment is needed in a navigation system, what reduces costs, simplifies the surgery and optimizes surgery time.

According to embodiments of the invention, numerous radiographic X-ray images for intra-operative curvature measurements are saved, thereby also saving radiation dose for the patient and reducing intra-operative imaging costs.

Preferred embodiments comprise one or more of the following features, which can be taken separately or together, either in partial combination or in full combination, with one or more of preceding objects of the invention.

Preferably, in a realization mode, said portion is a hollow having the shape and the size of said spinal correction rod. This way, the cut and bent spinal correction rod implant may be compared not only visually but also mechanically with the surgery planning tool, by inserting the spinal correction rod implant in the surgery planning tool.

Preferably, said hollow is a cavity. This way, inserting the spinal correction rod implant in the surgery planning tool will show each and every difference between the spinal correction rod implant and the surgery planning tool, since the spinal correction rod implant will need to fit exactly the surgery planning tool. This way, the surgery planning tool is more precise.

Preferably, in another embodiment, said hollow is a through hole. This way, inserting the spinal correction rod implant in the surgery planning tool will show most of the differences between the spinal correction rod implant and the surgery planning tool, while still managing a tool simpler to manufacture than the cavity tool.

Preferably, said elongated body comprises two hinged parts which are foldable over each other so as to reduce the length of said elongated body, said parts being hinged preferably in the middle of said elongated body. This way, the surgery planning tool is made less bulky and easier to store and transport.

Preferably, said portion includes two hollows having respectively the shape and the size of two spinal correction rods, and main curvature of one of said hollows is convex whereas main curvature of the other of said hollows is concave, and wherein said convex hollow has the shape and the size of a spinal correction rod adapted to be implemented on one side of patient spine whereas said concave hollow has the shape and the size of a spinal correction rod adapted to be implemented on the other side of patient spine. A single surgery control tool then advantageously deals with the two spinal correction rod implants simultaneously.

Preferably, in another realization mode, said elongated body as a whole has the shape and the size of said spinal correction rod. This way, the surgery planning tool is easier to manufacture and much less bulky therefore much easier to store and transport.

Preferably, said portion has the length and the curvature of said spinal correction rod. This way, the surgery planning tool is more precise and thereby more useful to the surgeon.

Preferably, in a realization mode, said surgery planning tool is made of plastic. This is a simple and cheap material, besides lowering the total weight of the surgery planning tool.

Preferably, said surgery planning tool is a 3D printed plastic rod. This is a simple way to manufacture a quite precisely dimensioned object.

Preferably, said 3D printed plastic rod is in 2 or 3 parts which can be fastened together, preferably via a quick quarter turn fastener. This way, the surgery planning tool is easier to manufacture and less bulky therefore easier to store and transport, when its different parts are separated from each other or from one another.

Preferably, in another realization mode, said surgery planning tool is made of resin, preferably of epoxy resin. This is a simple and cheap material, besides lowering the total weight of the surgery planning tool.

Preferably, said surgery planning tool is a resin rod manufactured by 3D photolithography. This is a simple way to manufacture a quite precisely dimensioned object.

Preferably, in another realization mode, said surgery planning tool is made of polyamide, preferably of PA2200. This is a simple and cheap material, besides lowering the total weight of the surgery planning tool.

Preferably, said surgery planning tool is a resin rod manufactured by selective laser sintering. This is a simple way to manufacture a quite precisely dimensioned object.

Preferably, said spinal correction rod is a patient specific spinal correction rod. This way, the surgery planning tool is more precisely adapted to the specific patient in the body of whom the spinal correction rod implant is to be implemented.

Preferably, said patient specific spinal correction rod includes one or more among following patient specific spinal corrections or modifications: Cobb angle correction, Kyphosis angle modification, Lordosis angle modification, Vertebral rotation correction. This way, most of important spinal corrections can be taken into account by the surgery planning tool.

Preferably, in a realization mode, said elongated body is two dimensional. This way, the surgery planning tool is easier to manufacture.

Preferably, in another realization mode, said elongated body is three dimensional. This way, the surgery planning tool is more precise and more representative of the spinal correction rod implant to be implemented in patient body.

Preferably, said surgery planning tool is a single use tool. This way, it can be personalized as much as possible, and thereby made as close as possible to the specific spinal correction rod implant to be implemented in the specific contemplated patient body, and so be made more precise and more useful to the surgeon, because it will not be reused for any other patient. Sterility is also more easily warranted this way.

Preferably, on said surgery planning tool are printed one or more among following information: a patient specific identification, a patient specific clinical parameter, a 3D orientation of said tool, a rod identification, an indication about over bending or under bending, if any. This way, the surgeon has at her or his disposal most of useful and needed information directly on the surgery planning tool, with no need for another complementary source of information for the specific patient to be operated.

Preferably, said spinal correction rod has the precise shape and the precise size of a spinal correction rod implant obtained from 3D spinal reconstruction got from two 2D X-ray patient images. This way, the surgery planning tool is more precise and more representative of the spinal correction rod implant to be implemented in patient body, and its manufacturing process has taken advantage of results got from the radiography process having been done before.

Preferably, said tool is sterilized. This way, it can be used by the surgeon, during intervention on patient body, without being a cause of sterilization problem or difficulty.

Preferably, said tool length ranges from 10 cm to 70 cm, preferably ranges from 20 cm to 50 cm. This way, the surgery planning tool can be manufactured on the same scale as the spinal correction rod implant, thereby making comparison simpler and more efficient for the surgeon.

Preferably, said surgery planning tool is over bended or under bended as compared to patient implanted spinal correction rod implant. This way, the surgery planning tool corresponds more precisely to the spinal correction rod implant, not in its original shape, but in its final shape when implemented, thereby integrating the counter effort exerted by the patient spine when submitted to the straightening effort of the spinal correction rod implant. This more precise surgery planning tool will be even more useful to the surgeon.

Further features and advantages of the invention will appear from the following description of embodiments of the invention, given as non-limiting examples, with reference to the accompanying drawings listed hereunder.

DETAILED DESCRIPTION OF THE INVENTION

Figure 1:
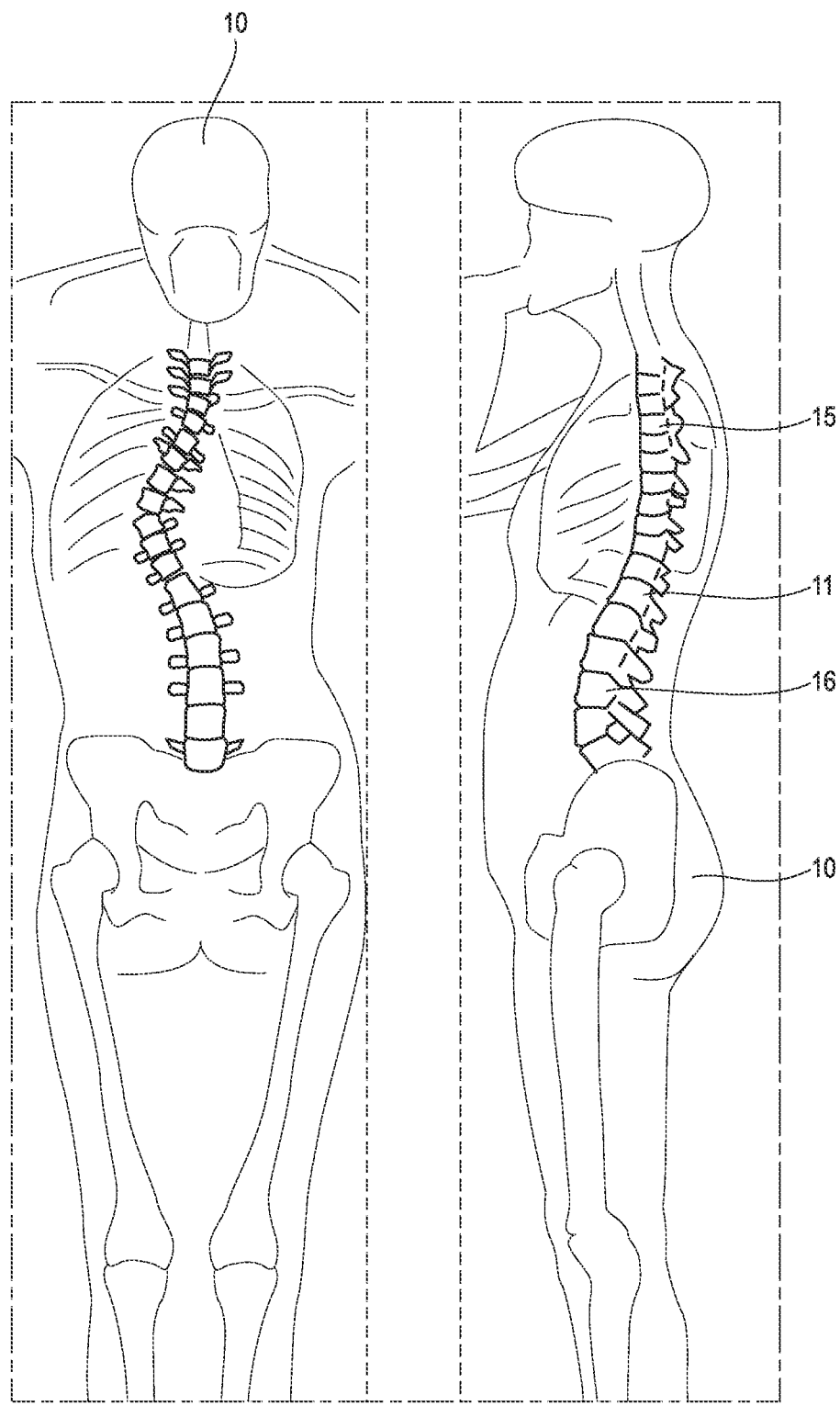
FIG. 1 shows an example of a patient radiography and 3D modeling, both frontal view on the left side and sagittal view on the right side, showing patient spine suffering from a scoliosis.

FIG. 1 shows an example of a patient radiography and 3D modeling, both frontal view on the left side and sagittal view on the right side, showing patient spine suffering from a scoliosis. The patient 10 can be seen as well as her or his patient vertebral spine 11.

On the left side of FIG. 1, when looking at the frontal view of the patient spine, if the patient was in good health, one should see a straight patient vertebral spine, which is not at all the case. On the contrary, patient vertebral spine 11 shows, in the frontal plane, a big curvature corresponding to an important scoliosis. This important scoliosis is to be corrected by implementing, respectively on both sides of this patient spine 11, two spinal correction rod implants which will straighten this curved patient spine 11.

On the right side of FIG. 1, when looking at the sagittal view of the patient spine, if the patient was in good health, one should see a patient vertebral spine corresponding to a typical kyphosis for upper part 15 of patient spine 11 and to a typical lordosis for lower part 16 of patient spine 11, what is not exactly the case. These incorrect kyphosis and lordosis are to be corrected by implementing, respectively on both sides of this patient spine 11, two spinal correction rod implants which will change the respective curvatures of kyphosis and lordosis of this patient spine 11.

Figure 2:
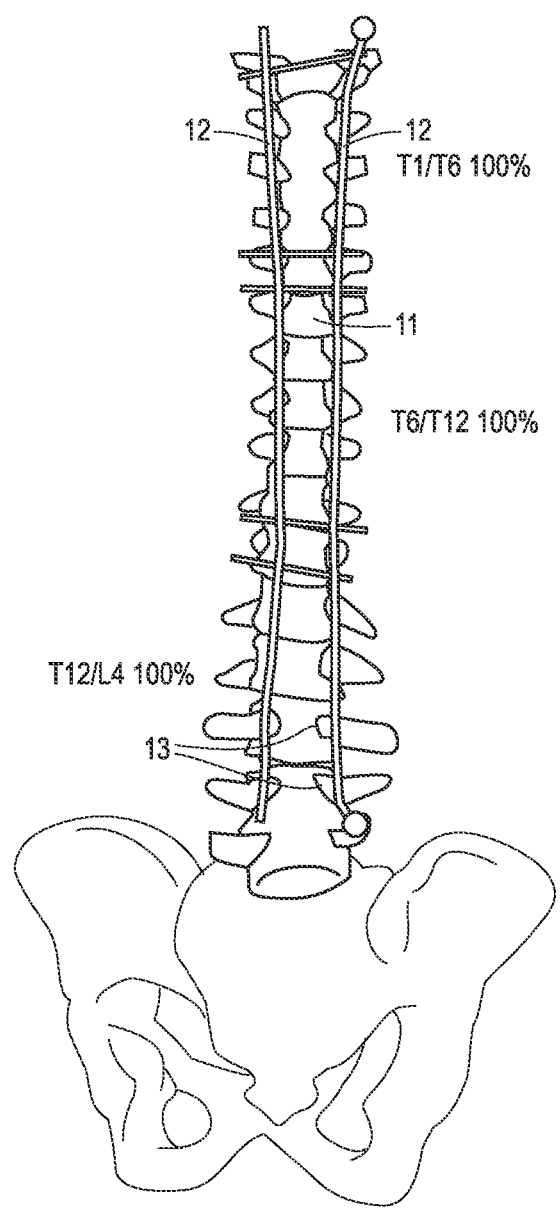
FIG. 2 shows an example of a 3D modeling, posterior view, showing patient spine previously suffering from a scoliosis but now straightened by two spinal correction rod implants.

FIG. 2 shows an example of a 3D modeling, posterior view, showing patient spine previously suffering from a scoliosis but now straightened by two spinal correction rod implants.

The important scoliosis, which could be seen on FIG. 1, was corrected by implementing, respectively on both sides of this patient spine 11, two spinal correction rod implants 12 and 13 which have straightened this curved patient spine 11. Both spinal correction rod implants 12 and 13 are fixed on patient spine 11 by screws 14. The screws 14 have been screwed in the vertebra of patient spine 11. The head of each screw 14 includes a slit in which the spinal correction rod implant 12 or 13 is held in place. Both spinal correction rod implants 12 and 13, being fixed on patient spine 11 by screws 14, and being straight and rigid because being made of metal, exert a constraint on patient spine 11, thereby straightening patient spine 11.

Figure 3:
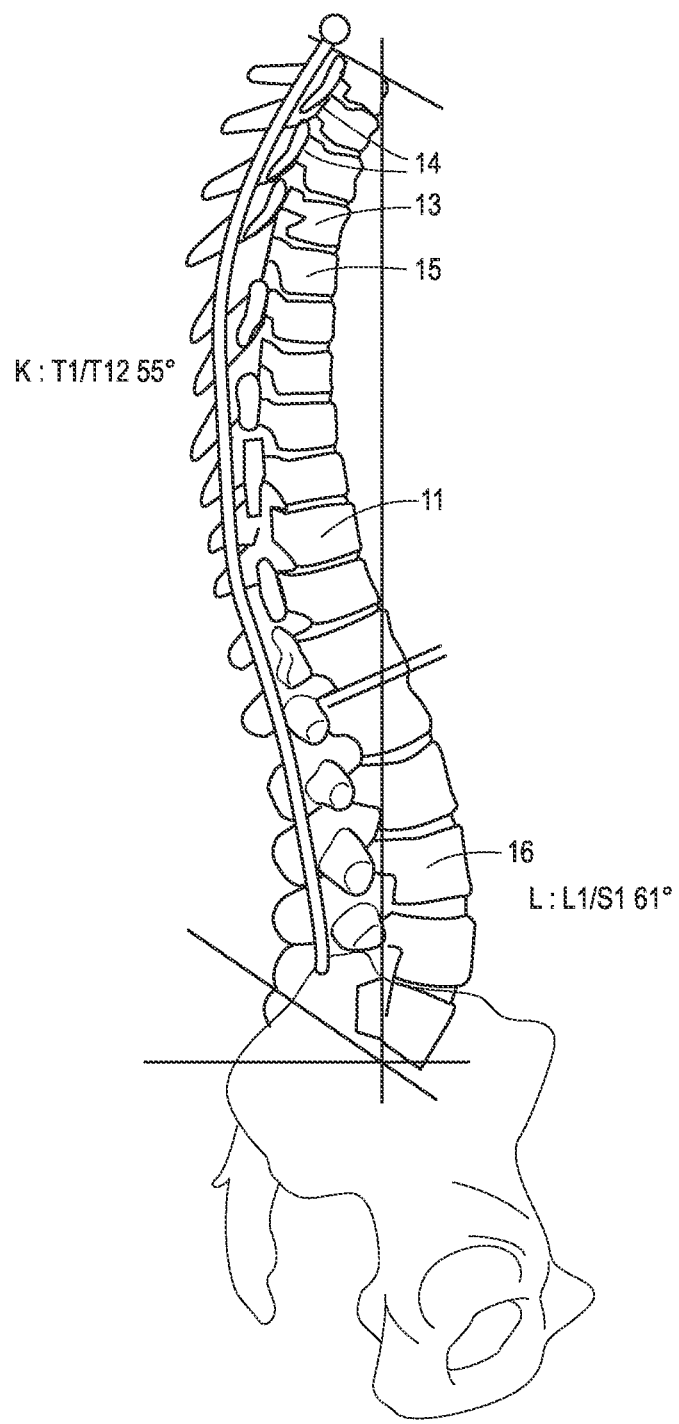
FIG. 3 shows an example of a 3D modeling, sagittal view, showing patient spine previously suffering from a scoliosis but now straightened by two spinal correction rod implants.

FIG. 3 shows an example of a 3D modeling, sagittal view, showing patient spine previously suffering from a scoliosis but now straightened by two spinal correction rod implants.

The incorrect kyphosis and lordosis, which could be seen on FIG. 1, were corrected by implementing, respectively on both sides of this patient spine 11, two spinal correction rod implants 12 and 13 (only spinal correction rod implant 13 can be seen on FIG. 3) which have changed the respective kyphosis and lordosis curvatures of this curved patient spine 11. Both spinal correction rod implants 12 and 13 are fixed on patient spine 11 by screws 14. The screws 14 have been screwed in the vertebra of patient spine 11. The head of each screw 14 includes a slit in which the spinal correction rod implant 12 or 13 is held in place. Both spinal correction rod implants 12 and 13, being fixed on patient spine 11 by screws 14, and being correctly curved and rigid because being made of metal, exert a constraint on patient spine 11, thereby changing and making correct the respective kyphosis and lordosis curvatures of respectively the upper part 15 and lower part 16 of this curved patient spine 11.

Figure 4A:
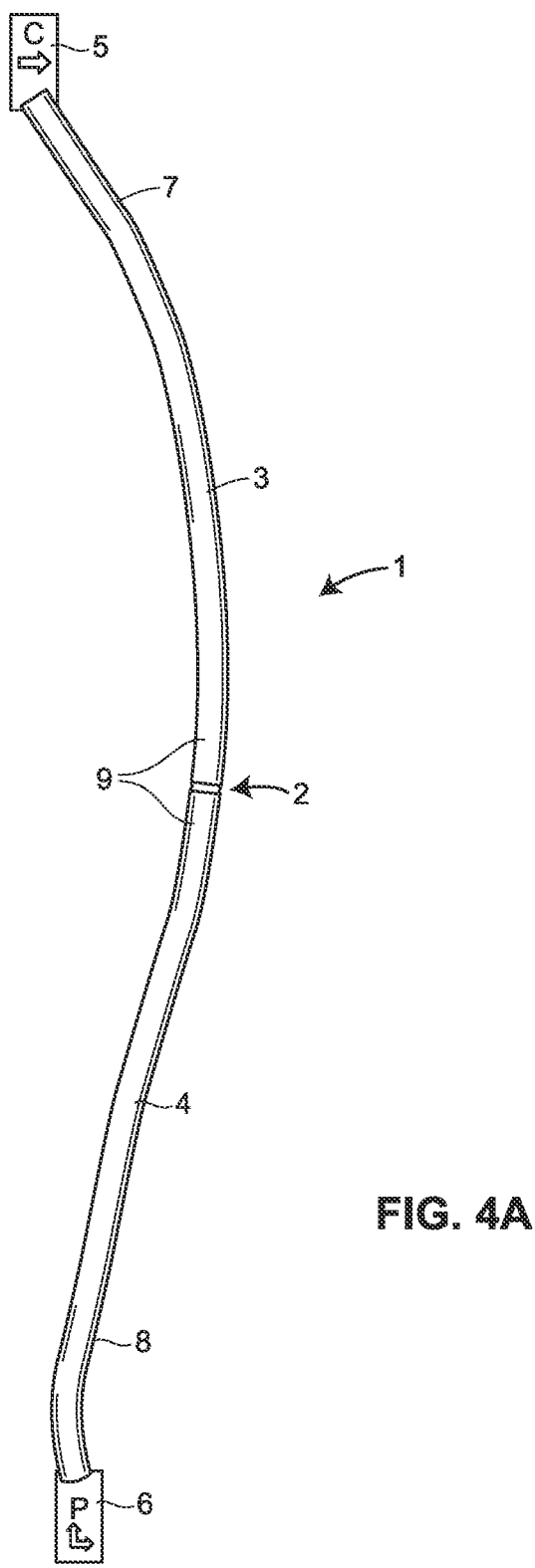
FIG. 4A shows an example of a surgery planning tool according to a first embodiment of the invention.

FIG. 4A shows an example of a surgery planning tool according to a first embodiment of the invention.

Once the surgery planning is made with planning software, the lengths and shapes of the rods are used to produce the planning templates which are the surgery planning tools. These planning templates are 3D printed and then sterilized, for instance with gamma ray sterilization, and sent to the hospital for the surgery.

The surgery planning tool 1 is no patient implant. The surgery planning tool 1 comprises an elongated body 9 which includes at least a portion having the shape and the size of a spinal correction rod. Here, this elongated body 9 as a whole has the shape and the size of the spinal correction rod implant it represents. This elongated body 9 has the length and the curvature of the spinal correction rod implant it represents.

The surgery planning tool 1 is a 3D (three dimensional) printed plastic rod which is in two parts, an upper part 3 and a lower part 4, which can be fastened together, via a quick quarter turn fastener 2.

The surgery planning tool 1, which is the planning template, can have a length too long to be printed in one part, thus this template can be printed in two parts 3 and 4, and the two parts 3 and 4 are assembled during the surgery preparation using a printed fixation part 2 such as a quick quarter turn fastener.

On the end of upper part 3 there is a piece of information 7 about patient and/or patient spinal correction which has been etched in the plastic. On the end of lower part 4 there is a piece of information 8 about patient and/or patient spinal correction which has been etched in the plastic.

At upper end of surgery tool 1, there is an upper plate 5 which first indicates it is the upper end and which second allows for the surgeon to more easily manipulate the surgery planning tool 1, by holding this upper plate 5 firmly and precisely between her or his fingers, the plan of this upper plate 5 being in the sagittal plane of the surgery planning tool 1. At lower end of surgery tool 1, there is an lower plate 6 which first indicates it is the lower end and which second allows for the surgeon to more easily manipulate the surgery planning tool 1, by holding this lower plate 6 firmly and precisely between her or his fingers, the plan of this lower plate 6 being in the sagittal plane of the surgery planning tool 1 and being in the same plan as the upper plate 5.

By visually comparing the straight and long original rod with this surgery planning tool 1, the surgeon first cuts the original rod either at the same length as this surgery planning tool 1 or slightly longer, and second bends the cut rod so that this rod presents the same curvatures, kyphosis and lordosis, as the surgery planning tool 1. Afterwards, if applicable, the surgeon may again cut the already cut and bent rod at the same length as this surgery planning tool 1. When this cut and bent rod presents the same length and the same curvature as this surgery planning tool 1, it can be implemented as a spinal correction rod implant within patient body.

Figure 4B:
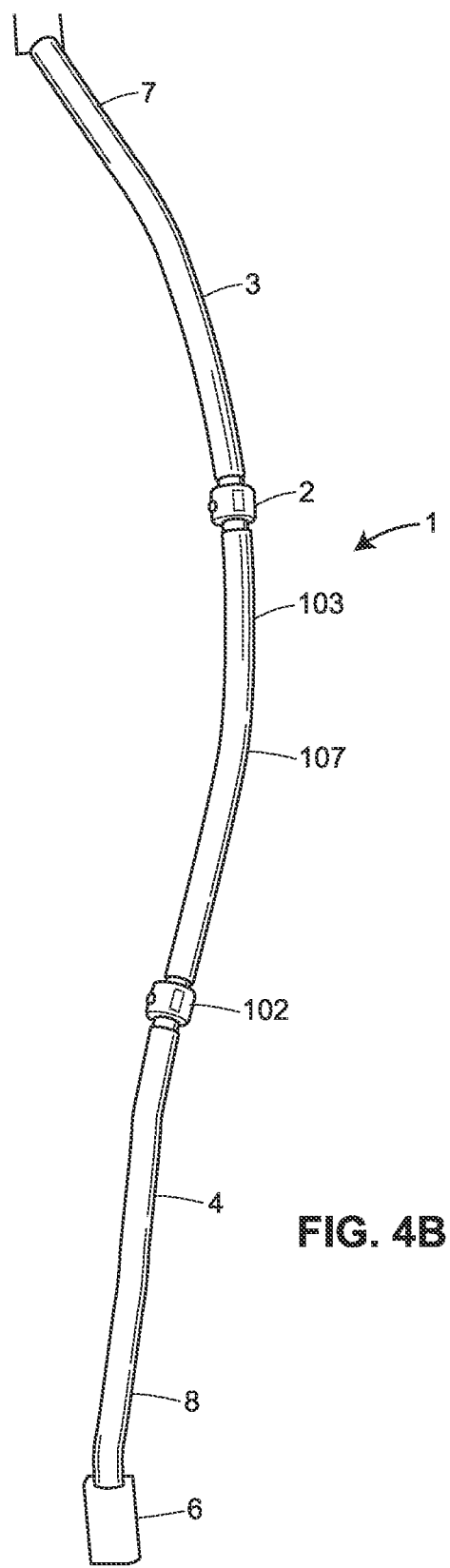
FIG. 4B shows another example of a surgery planning tool according to a first embodiment of the invention.

FIG. 4B shows another example of a surgery planning tool according to a first embodiment of the invention.

The surgery planning tool 1 comprises an elongated body 9 which includes at least a portion having the shape and the size of a spinal correction rod. Here, this elongated body 9 as a whole has the shape and the size of the spinal correction rod implant it represents. This elongated body 9 has the length and the curvature of the spinal correction rod implant it represents.

The surgery planning tool 1 is a 3D (three dimensional) printed plastic rod which is in three parts, an upper part 3, an intermediate part 103 and a lower part 4, which can be fastened together, via two quick quarter turn fasteners 2 and 102. Upper part 3 and intermediate part 103 can be fastened together, via a two quick quarter turn fastener 2. Intermediate part 103 and lower part 4 can be fastened together, via a two quick quarter turn fastener 102.

The surgery planning tool 1, which is the planning template, can have a length too long to be printed in one part, thus this template can be printed in three parts 3, 103 and 4, and the three parts 3, 103 and 4 are assembled during the surgery preparation using printed fixation parts 2 and 102 such as quick quarter turn fasteners.

On the end of upper part 3 there is a piece of information 7 about patient and/or patient spinal correction which has been etched in the plastic. On the end of lower part 4 there is a piece of information 8 about patient and/or patient spinal correction which has been etched in the plastic. On the middle of intermediate part 103 there is a piece of information 107 about patient and/or patient spinal correction which has been etched in the plastic.

At upper end of surgery tool 1, there is an upper plate 5 which first indicates it is the upper end and which second allows for the surgeon to more easily manipulate the surgery planning tool 1, by holding this upper plate 5 firmly and precisely between her or his fingers, the plan of this upper plate 5 being in the sagittal plane of the surgery planning tool 1. At lower end of surgery tool 1, there is an lower plate 6 which first indicates it is the lower end and which second allows for the surgeon to more easily manipulate the surgery planning tool 1, by holding this lower plate 6 firmly and precisely between her or his fingers, the plan of this lower plate 6 being in the sagittal plane of the surgery planning tool 1 and being in the same plan as the upper plate 5.

Figure 5:
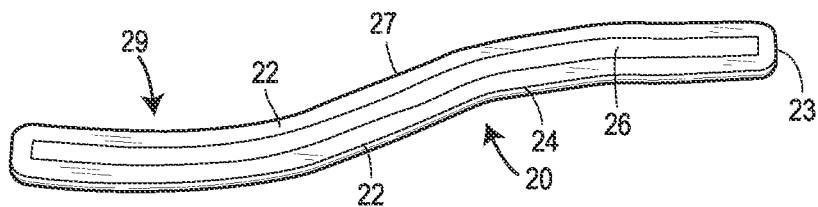
FIG. 5 shows an example of a surgery planning tool according to a second embodiment of the invention.

FIG. 5 shows an example of a surgery planning tool according to a second embodiment of the invention.

The surgery planning tool 20 comprises an elongated body 29 which includes a hollow 21 formed by a cavity 21 having the shape and the size, and more precisely the curvature and the length, of a spinal correction rod implant. The elongated body 29 of the surgery planning tool 20 has a shape complementary to spinal correction rod implant. The spinal correction rod implant can then be put within the cavity 21 and rests against the back of the cavity 21, allowing for the surgeon to see if its shape and size are satisfactory or if this spinal correction rod implant still needs cutting and/or bending to be performed by the surgeon. This cavity 21 is surrounded by an edge 22. At both extremities of the cavity 21 are located ends 23 of this edge 22. On this edge 22 are printed one or more pieces of information 27 containing information about the patient and about the spinal correction rod implant to be implemented in this patient spine by the surgeon. The surgeon will get two such surgery planning tools 20, one for each spinal correction rod implant.

Figure 6A:
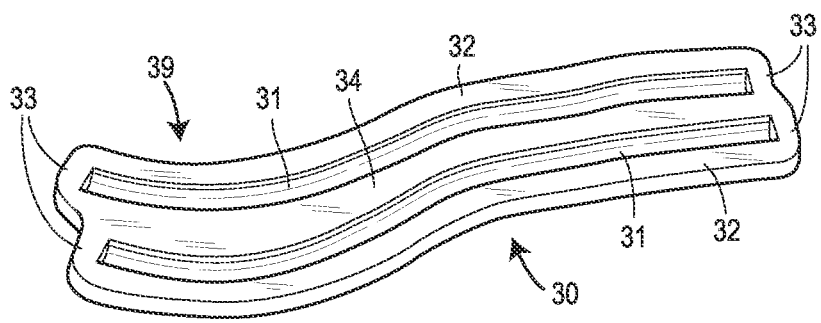
FIG. 6A shows an example of a front view of a surgery planning tool according to a third embodiment of the invention.

FIG. 6A shows an example of a front view of a surgery planning tool according to a third embodiment of the invention.

The surgery planning tool 30 comprises an elongated body 39 which includes two hollows 31 formed by two cavities 31 having the shape and the size, and more precisely the curvature and the length, respectively of two spinal correction rod implants to be implemented respectively on both sides of the patient spine. The elongated body 39 of the surgery planning tool 30 has a shape complementary to both spinal correction rod implants. Each spinal correction rod implant can then be put within its cavity 31 and rests against the back of its cavity 31, allowing for the surgeon to see if its shape and size are satisfactory or if this spinal correction rod implant still needs cutting and/or bending to be performed by the surgeon. These cavities 31 are surrounded by an edge 32. A wall 34 is located between both cavities 31. At both extremities of these cavities 31 are located ends 33 of this edge 32. On this edge 32 is printed no information. The information about the patient and about the spinal correction rod implant to be implemented in this patient spine by the surgeon will be provided on another support like a sheet of paper being packed in the same package as the surgery planning tool 30.

Figure 6B:
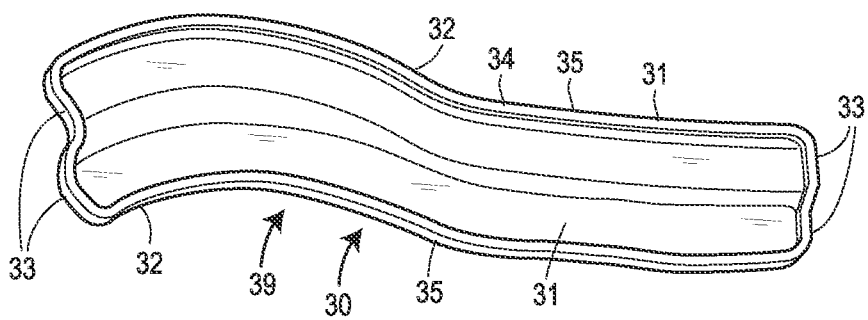
FIG. 6B shows an example of a back view of a surgery planning tool according to a third embodiment of the invention.

FIG. 6B shows an example of a back view of a surgery planning tool according to a third embodiment of the invention.

A flange 35 surrounds the edge 32. This flange 35 is sufficiently protruding so that the surgery planning tool 30 back rests on this flange 35 and not on the back of the cavities 31, although the cavities 31 have a given depth, when this surgery planning tool 30 rests on its back.

Figure 7A:
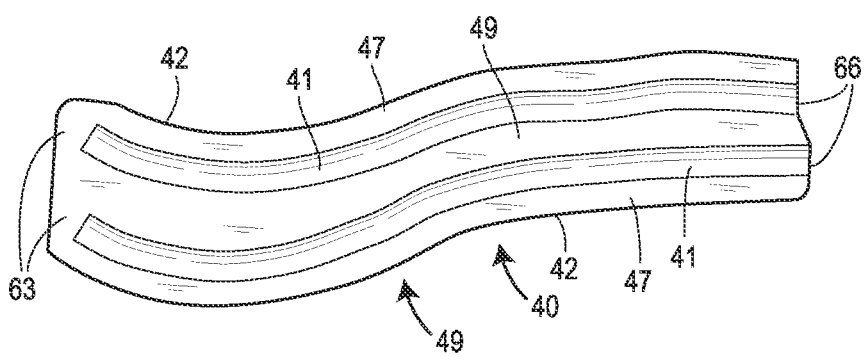
FIG. 7A shows an example of a front view of a surgery planning tool according to a fourth embodiment of the invention.

FIG. 7A shows an example of a front view of a surgery planning tool according to a fourth embodiment of the invention.

The surgery planning tool 40 comprises an elongated body 49 which includes two hollows 41 formed by two cavities 41 having the shape and the size, and more precisely the curvature and the length, respectively of two spinal correction rod implants to be implemented respectively on both sides of the patient spine. The elongated body 49 of the surgery planning tool 40 has a shape complementary to both spinal correction rod implants. Each spinal correction rod implant can then be put within its cavity 41 and rests against the back of its cavity 41, allowing for the surgeon to see if its shape and size are satisfactory or if this spinal correction rod implant still needs cutting and/or bending to be performed by the surgeon. These cavities 41 are surrounded by an edge 42. A wall 44 is located between both cavities 41. At only one extremity of these cavities 41 is located an end 43 of this edge 42. At the other extremity of these cavities 41 is located no end 43 of this edge 42, but an opening 46 of this edge 42. There is a stop 43, for stopping the spinal correction rod implants, only at one extremity of these cavities 41 and not at the other extremity. On this edge 42 are printed one or more pieces of information 47 containing information about the patient and about the spinal correction rod implant to be implemented in this patient spine by the surgeon.

Figure 7B:
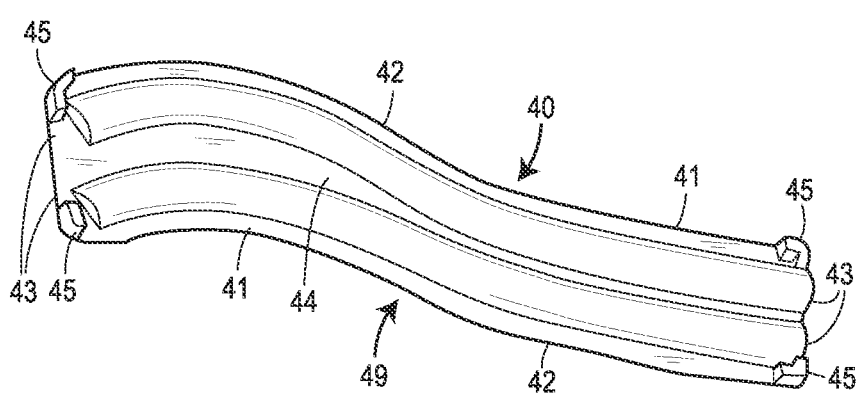
FIG. 7B shows an example of a back view of a surgery planning tool according to a fourth embodiment of the invention.

FIG. 7B shows an example of a back view of a surgery planning tool according to a fourth embodiment of the invention.

Four corners 45 surround the edge 42. These four corners 45 are sufficiently protruding so that the surgery planning tool 40 back rests on these corners 45 and not on the back of the cavities 41, although the cavities 41 have a given depth, when this surgery planning tool 40 rests on its back. Four corners 45 are more stable than a flange 35 as on FIG. 6B.

Figure 8:
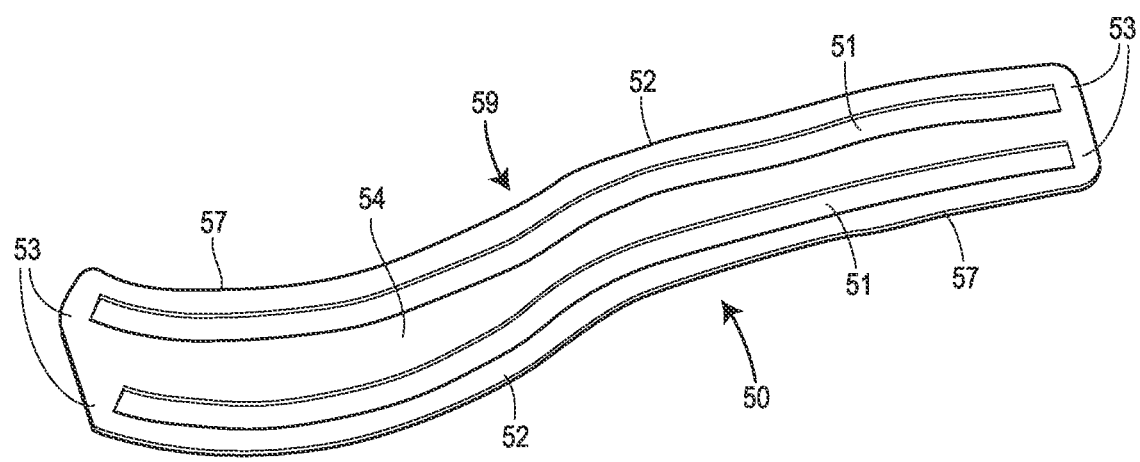
FIG. 8 shows an example of a surgery planning tool according to a fifth embodiment of the invention.
Figure 9:
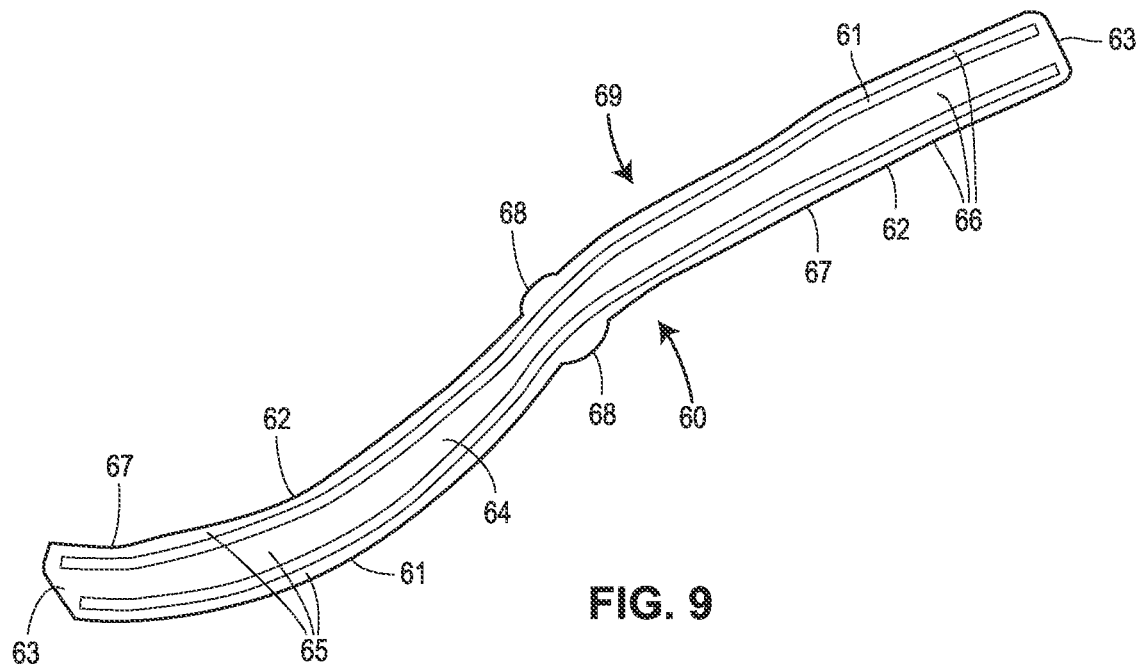
FIG. 9 shows an example of a surgery planning tool according to a sixth embodiment of the invention.

Surgery planning tools 20, 30 and 40, represented on FIGS. 5, 6A, 6B, 7A and 7B, allow for the surgeon to check more precisely the correctness of length and curvature of the spinal correction rod implants, than the surgery planning tools 50 and 60, represented on FIGS. 8 and 9, thanks to the existing back of the cavities 21, 31 and 41.

FIG. 8 shows an example of a surgery planning tool according to a fifth embodiment of the invention.

The surgery planning tool 50 comprises an elongated body 59 which includes two hollows 31 formed by two through holes 51 having the shape and the size, and more precisely the curvature and the length, respectively of two spinal correction rod implants to be implemented respectively on both sides of the patient spine. The elongated body 59 of the surgery planning tool 50 has a shape partially complementary to both spinal correction rod implants. Each spinal correction rod implant can then be put just in its through hole 51 without going completely through the elongated body 59, allowing for the surgeon to see if its shape and size are satisfactory or if this spinal correction rod implant still needs cutting and/or bending to be performed by the surgeon. These through holes 51 are surrounded by an edge 52. A wall 54 is located between both through holes 51. At both extremities of these through holes 51 are located ends 53 of this edge 52. On this edge 52 are printed one or more pieces of information 57 containing information about the patient and about the spinal correction rod implant to be implemented in this patient spine by the surgeon.

FIG. 9 shows an example of a surgery planning tool according to a sixth embodiment of the invention.

The surgery planning tool 60 comprises an elongated body 69 which includes two hollows 61 formed by two through holes 61 having the shape and the size, and more precisely the curvature and the length, respectively of two spinal correction rod implants to be implemented respectively on both sides of the patient spine. The elongated body 69 of the surgery planning tool 60 has a shape partially complementary to both spinal correction rod implants. Each spinal correction rod implant can then be put just in its through hole 61 without going completely through the elongated body 69, allowing for the surgeon to see if its shape and size are satisfactory or if this spinal correction rod implant still needs cutting and/or bending to be performed by the surgeon. These through holes 61 are surrounded by an edge 62. A wall 64 is located between both through holes 61. At both extremities of these through holes 61 are located ends 63 of this edge 62. On this edge 62 are printed one or more pieces of information 67 containing information about the patient and about the spinal correction rod implant to be implemented in this patient spine by the surgeon. The elongated body 69 comprises two hinged parts 65 and 66 which are foldable over each other so as to reduce the length of said elongated body 69, said parts 65 and 66 being hinged preferably in the middle of said elongated body 69. There is a hinge 68 between said parts 65 and 66.

Surgery planning tools 50 and 60, represented on FIGS. 8 and 9, are less bulky and easier to conceive, than the surgery planning tools 20, 30 and 40, represented on FIGS. 5, 6A, 6B, 7A and 7B, thanks respectively to the flatness of these surgery planning tools 50 and 60, and to their only partially complementary shape to the spinal correction rod implants.

The invention has been described with reference to preferred embodiments. However, many variations are possible within the scope of the invention.

The invention claimed is:

1. A method comprising:
a first step of obtaining two 2D X-ray images of a spine;
after the first step, performing a second step of making a patient specific 3D spinal reconstruction from said two 2D X-ray patient images;
after the second step, performing a third step of determining a patient specific spinal correction;
after the third step, performing a fourth step of manufacturing a surgery planning tool having a shape of a patient specific spinal correction rod implant that is over bended or under bended as compared to a final shape of the spinal correction rod implant after being implanted;
visually comparing a shape of the spinal correction rod implant with the shape, and bending the spinal correction rod implant so that the spinal correction rod implant presents curvatures corresponding to the shape; and
implanting the spinal correction rod implant such that it assumes the final shape, such that, as a result of the final shape, a straightening effort is exerted on the spine to align with the patient specific spinal correction.

* * * * *